(12) United States Patent
Hawryluk (10) Patent No.: US 10,543,473 B2
(45) Date of Patent: Jan. 28, 2020

(54) CONTROLLING LOCAL FLUID AGE IN A STIRRED REACTOR

(71) Applicant: NOVA Chemicals (International) S.A., Fribourg (CH)

(72) Inventor: Andrew Hawryluk, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 261 days.

(21) Appl. No.: 15/319,414

(22) PCT Filed: Jun. 4, 2015

(86) PCT No.: PCT/IB2015/054247
§ 371 (c)(1),
(2) Date: Dec. 16, 2016

(87) PCT Pub. No.: WO2015/198176
PCT Pub. Date: Dec. 30, 2015

(65) Prior Publication Data
US 2017/0136436 A1 May 18, 2017

Related U.S. Application Data

(60) Provisional application No. 62/016,156, filed on Jun. 24, 2014.

(51) Int. Cl.
| | | |
|---|---|---|
| *B01F 7/16* | (2006.01) | |
| *B01J 19/00* | (2006.01) | |
| *B01F 15/00* | (2006.01) | |
| *B01J 19/18* | (2006.01) | |
| *G01N 21/64* | (2006.01) | |
| *B01F 7/22* | (2006.01) | |
| *C08F 2/01* | (2006.01) | |
| *G01F 1/708* | (2006.01) | |

(52) U.S. Cl.
CPC ............ *B01J 19/0066* (2013.01); *B01F 7/22* (2013.01); *B01F 15/00857* (2013.01); *B01F 15/00922* (2013.01); *B01J 19/18* (2013.01); *C08F 2/01* (2013.01); *G01F 1/7086* (2013.01); *G01N 21/6456* (2013.01); *B01F 2215/0036* (2013.01); *B01F 2215/0049* (2013.01); *B01F 2215/0404* (2013.01); *B01J 2219/00166* (2013.01); *B01J 2219/00761* (2013.01)

(58) Field of Classification Search
CPC ...................................................... B01F 7/1675
USPC ................................................... 366/142, 143
See application file for complete search history.

(56) References Cited

U.S. PATENT DOCUMENTS

| | | | |
|---|---|---|---|
| 2,825,721 A | 3/1958 | Hogan et al. | |
| 3,023,203 A | 2/1962 | Dye | |
| 3,622,251 A | 11/1971 | Allen | |
| 3,704,287 A | 11/1972 | Johnson | |
| 4,011,382 A | 3/1977 | Levine et al. | |
| 4,100,105 A | 7/1978 | Levine et al. | |
| 5,324,109 A * | 6/1994 | Johari ................... | B01F 3/0865 366/152.1 |
| 5,434,116 A | 7/1995 | Sone et al. | |
| 5,554,775 A | 9/1996 | Krishnamurti et al. | |
| 5,637,659 A | 6/1997 | Krishnamurti et al. | |

OTHER PUBLICATIONS

Danckwerts, P.V.; Local Residence-Times in Continuous-Flow Systems; Chemical Engineering Science, 1958, vol. 9, Pergamon Press Ltd. pp. 78-79.

Crimaldi, J.P.; Planar Laser Induced Fluorescence in Aqueous Flows; Experiments in Fluids 44 (2008); Springer-Verlag; Received: Nov. 14, 2007/Revised: Mar. 17, 2008/Accepted: Mar. 18, 2008/ Published online: Apr. 4, 2008; pp. 851-863.

* cited by examiner

*Primary Examiner* — David L Sorkin
(74) *Attorney, Agent, or Firm* — Julie L. Heinrich (57) ABSTRACT

In a stirred tank chemical reactor the mean age of the reactor contents affects a number of properties of the product, including for example the homogeneity of the product. The mean average age of the reactor contents can be determined by constructing a transparent model of the reactor and filling it with a fluid containing a fluorescent dye and having flow properties comparable to those of the reactor in use. A light is shone on the fluid as it is stirred under reaction conditions and a clear fluid flow into the model. Pictures are taken of the reactor contents and the mean fluid age of the contents of the model are determined relative to the exit age of the contents. This approach can be applied to determine for example which reactor ports to use, what agitator to use, what flow rates to use to improve reactor function.

12 Claims, 6 Drawing Sheets

CONTROLLING LOCAL FLUID AGE IN A STIRRED REACTOR

TECHNICAL FIELD

The present invention relates to a method to control the age of a fluid, preferably liquid as it passes through a stirred tank reactor. There are a number of situations where it is desirable to know how long it takes for a fluid to pass through a stirred, fluid filled reactor. This has implications for the homogeneity of the product

BACKGROUND ART

The paper "Local residence-times in continuous flow systems", P. V. Danckwerts, Chemical Engineering Science, 1958, Vol. 9, pp. 78-79, Pergamon Press Ltd. discusses the theory of local fluid ages and determining an average age in a continuous flow systems as an indication of the degree of stagnation of the material at a point in the system.

Although the patent literature is replete with references to residence time and ageing of reactants there is very little patent literature on methods to achieve appropriate local residence times in a continuous stirred tank reactor.

DISCLOSURE OF INVENTION

The present invention provides a process for operating a fluid-filled continuous stirred tank reactor so that the local age of the reactor contents normalized to the exit age is from 0.5 to 1.3.

In a further embodiment the agitator is selected from the group consisting of auger agitators, anchor agitators, radial blade turbine, pitched blade turbine, hydrofoil impeller, or a hybrid impeller comprising one or more of these elements.

In a further embodiment the process is a polymerization process.

In a further embodiment the fluid is liquid.

In a further embodiment the liquid is selected from the group consisting of one or more $C_{3-8}$ saturated hydrocarbons.

In a further embodiment the polymerization is a polymerization of one or more $C_{2-8}$ alpha olefins.

In a further embodiment the alpha olefins are selected from the group consisting of ethylene, propylene, butene, hexene, and octene.

In a further embodiment the local age of the reactor contents normalized to the exit age is from 0.5 to 1.3.

In a further embodiment the average normalized fluid age in the reactor is from 0.8 to 1.0.

In a further embodiment the coefficient of variance (standard deviation/mean) is from 0.01 to 0.10.

In a further embodiment the coefficient of variance (standard deviation/mean) is from 0.01 to 0.06.

In a further embodiment the catalyst for the polymerization is selected form the group consisting of single site catalysts, Ziegler-Natta catalysts, and chrome catalysts.

In a further embodiment the process is operated at a pressure from 5 to 20 MPa.

In a further embodiment the process is operated at a temperature from 130° C. to 220° C.

In a further embodiment the present invention provides a method to rank the efficiency of the operation of two or more CSTRs producing the same product comprising preparing transparent models of each reactor, including the agitator which may not be transparent, filling the model with a transparent liquid containing a dye, starting the agitator, washing the dye out of the reactor by introducing a flow of un-dyed liquid into the reactor, shining a laser (1 in FIG. 1) into the reactor while the dye is being washed out, and capturing the images using a digital camera, normalizing the images to determine the a local age of the reactor contents normalized to the exit age and coefficient of variance (CoV) for each CSTR, and comparing the values.

In a further embodiment the present invention provides a method for determining the transferability of manufacturing processes from one CSTR to another CSTR comprising preparing transparent models of each reactor, including the agitator which may not be transparent, filling the model with a transparent liquid containing a dye, starting the agitator, washing the dye out of the reactor by introducing a flow of un-dyed liquid into the reactor, shining a laser into the reactor while the dye is being washed out, and capturing the images using a digital camera, normalizing the images determining the a local age of the reactor contents normalized to the exit age and coefficient of variance (CoV) for each CSTR, and comparing the values and determining what operational changes need to be made to bring the values into conformity.

DETAILED DESCRIPTION

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Symbols

In the equations, figures, and the specification the following symbols have the following meanings:

$\tau$ (tau) is the residence time or the holdup time of the fluid in the reactor.

$\theta_{95}$ is the blend time or the bulk mixing time in the reactor.

t is time.

N is the agitator speed.

Re is the impeller Reynolds number.

Continuous stirred tank reactors (CSTR) may be used in a broad range of applications, for example potentially from condiments to polymerizations such as the polymerization of alpha olefins. For product consistency, particularly in an olefin polymerization, it is important that the local fluid age in the tank be reasonably consistent.

In the construction of a CSTR typically a number of inlets and outlets are built into the base design. However, typically only a limited number of inlets are actually used (one or two) in the installed reactor. For a given agitator system it is desirable to determine the effect of using different inlets on the relative homogeneity of the reactor contents, preferably prior to reactor installation. If the reactor is being designed or installed it is possible to determine which of the potential inlet locations would be useful to improve reactor homogeneity.

In the alternative for a given reactor inlet configuration it is desirable to understand the effect of different agitators on the relative homogeneity of the reactor contents.

In chemically reactive systems such polymerization it is important to know if there are zones of stagnation ("dead zones") in a reactor. It is also desirable to be able to estimate the relative interaction between catalyst kinetics and mixing efficiency. Zones of poor mixing are undesirable for highly active catalyst systems. This may introduce heterogeneity into the final product. By selecting a catalyst having slower kinetics the inhomogeneity of the product may be reduced.

As noted above, Danckwerts published the theory of local fluid ages. While the theory appears relatively straightforward, the issues arise in the application of the theory to a reactor.

Figure 1:
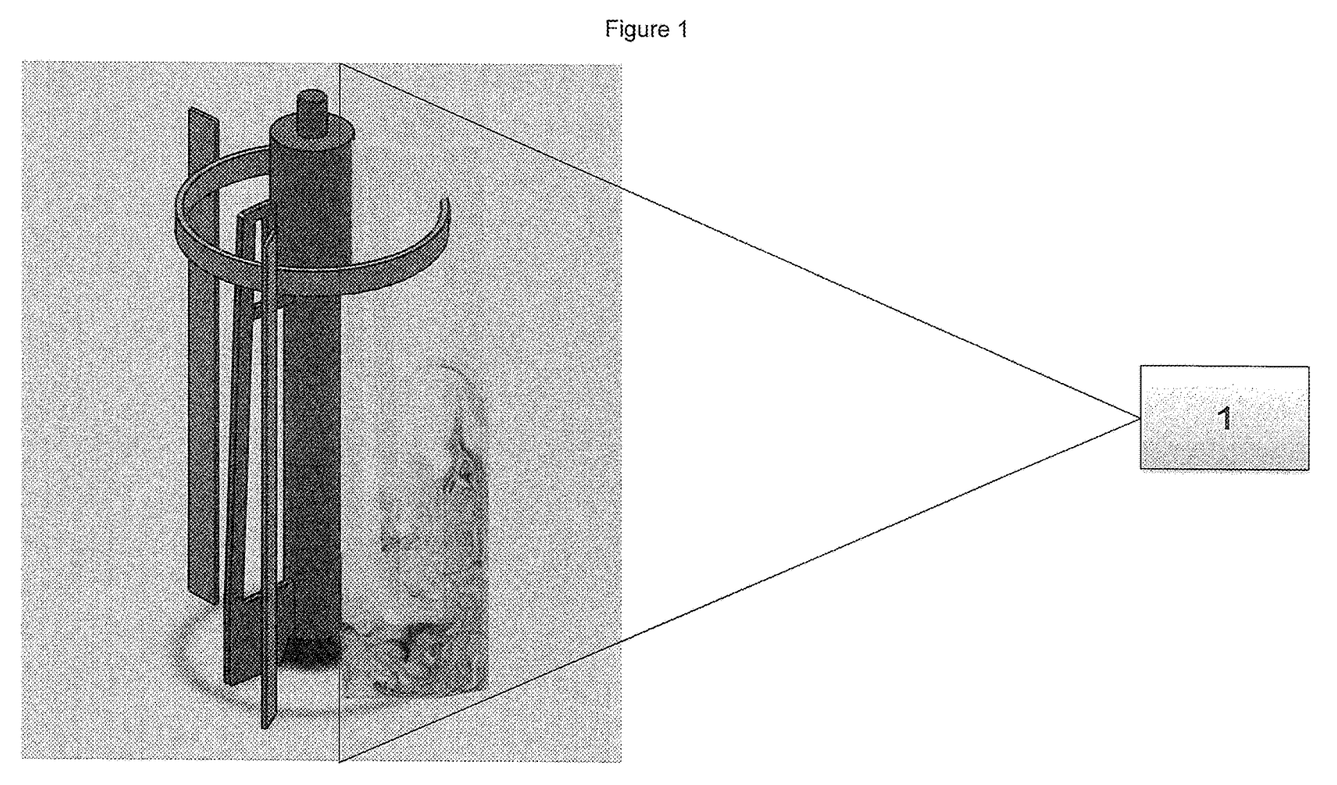
FIG. 1 is a schematic diagram of how the experiments were conducted. (this is slide 5)
Figure 2:
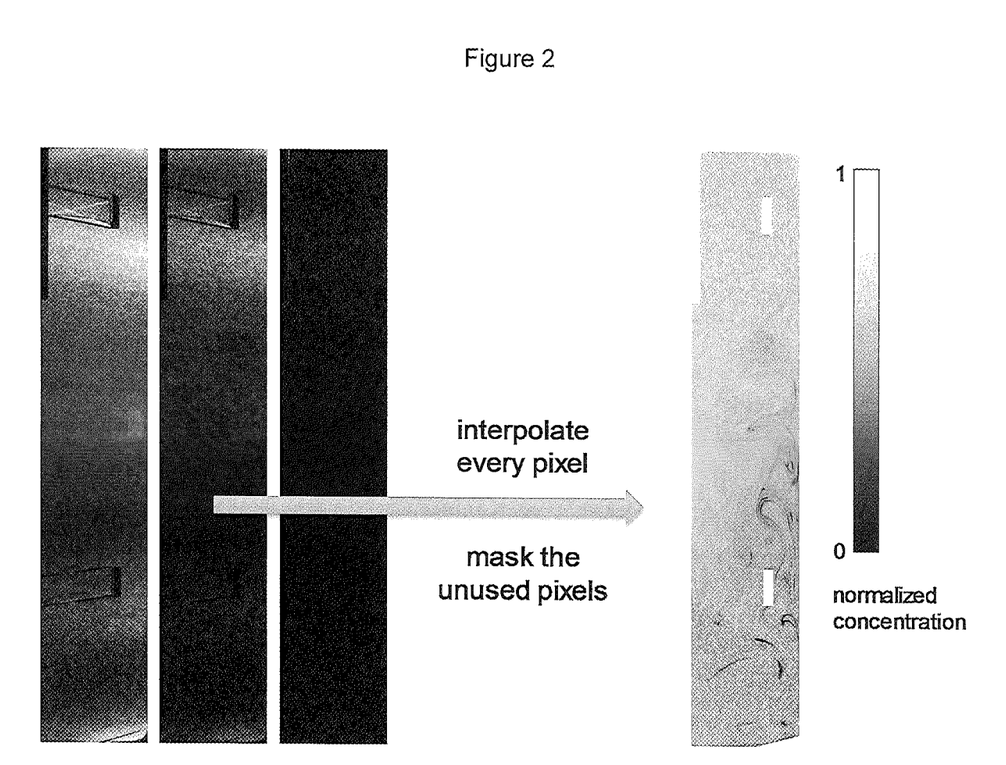
FIG. 2 is a schematic diagram illustrating how to convert the pictures to a normalized concentration (this is slide 7).
Figure 3:
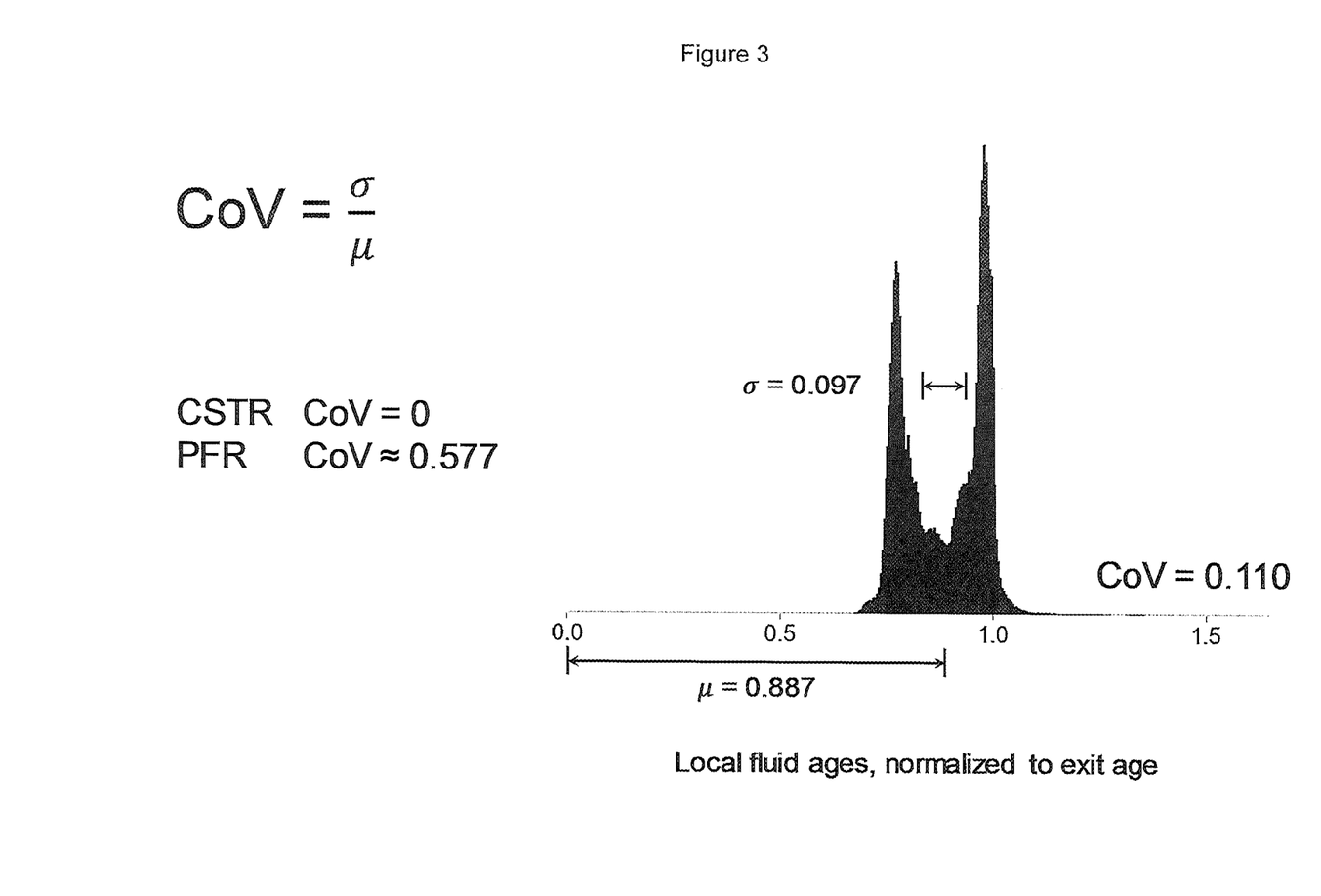
FIG. 3 shows how local fluid ages normalized to the exit age and the coefficient of variance can be used to quantify the inhomogeneity of a reactor.
Figure 4:
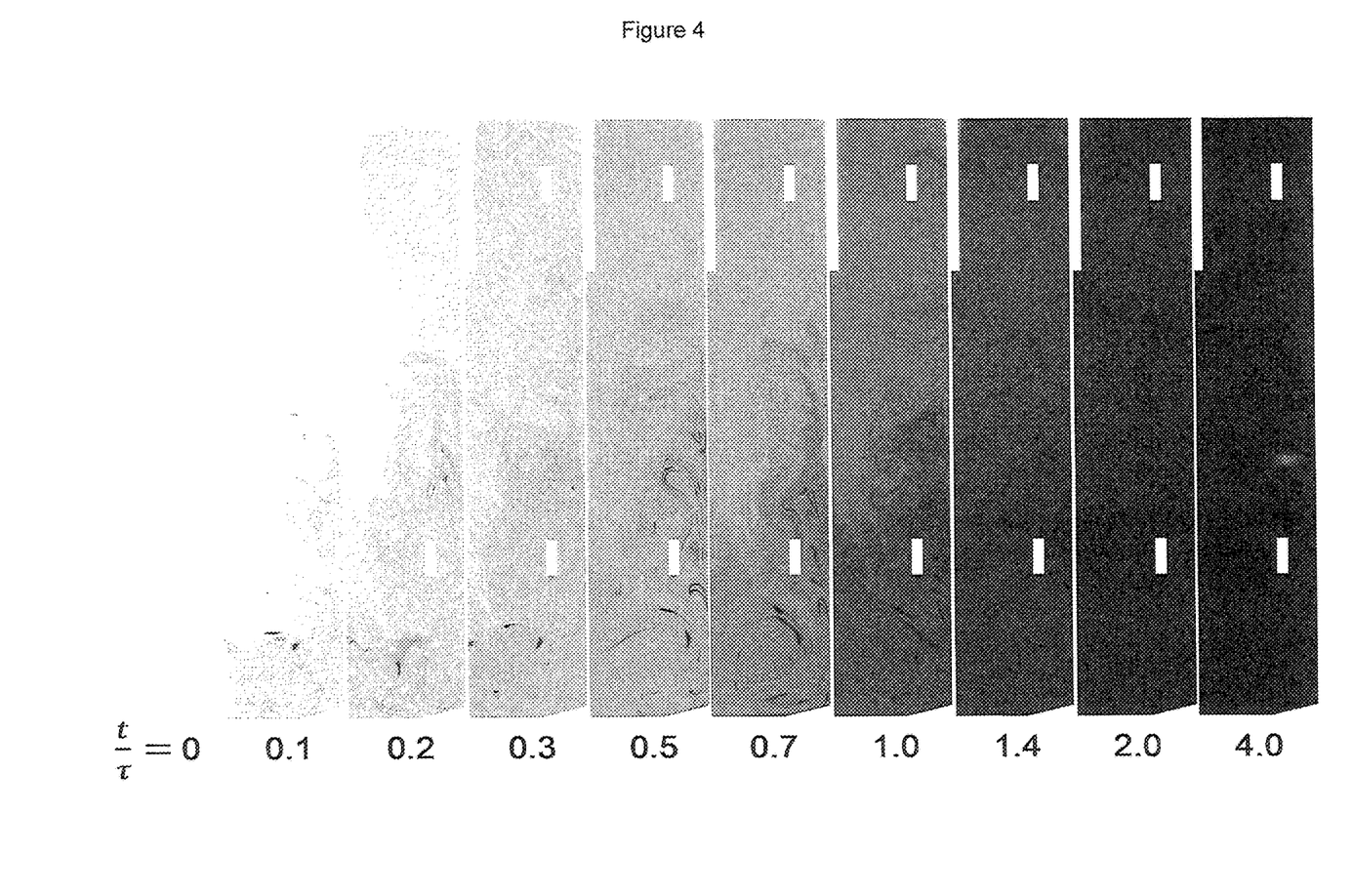
FIG. 4 shows progressive mixing in the reactor in experiment 1.

One method is to prepare a transparent scale model of the reactor in question including the agitator design and a number of alternate inlet ports. The reactor is filled with a test fluid that contains a uniform concentration of a tracer dye which fluoresces under a known wavelength of incident light, such as sodium fluorescein. The fluid is typically an aqueous gylcerol solution chosen to produce the desired impeller Reynolds number. A flow of undyed test fluid is commenced through the reactor with the agitator running introducing a step change in concentration. While the dye is washed out of the reactor and during mixing, a laser whose wavelength causes the dye to fluoresce at a different wavelength enters the reactor as a plane of light. This is schematically shown in FIG. 1. A digital camera captures images of the dye during the experiment, using a colored filter to block the incident laser light.

At the beginning of the experiment (t=0) the concentration in the reactor is known but typically normalized to 1. At the end of the experiment the (i.e. t=6 $\tau$) the concentration in the reactor is 0. The normalized concentration of any pixel in the experiment may be determined by a linear interpolation formula:

$$C(x,t)=[I(x,t)-I(x,t=\infty)]/[I(x,t=0)-I(x,t=\infty)]$$

where C is the normalized concentration, x is the pixel location, and I is the light intensity measured by the camera.

Figure 5:
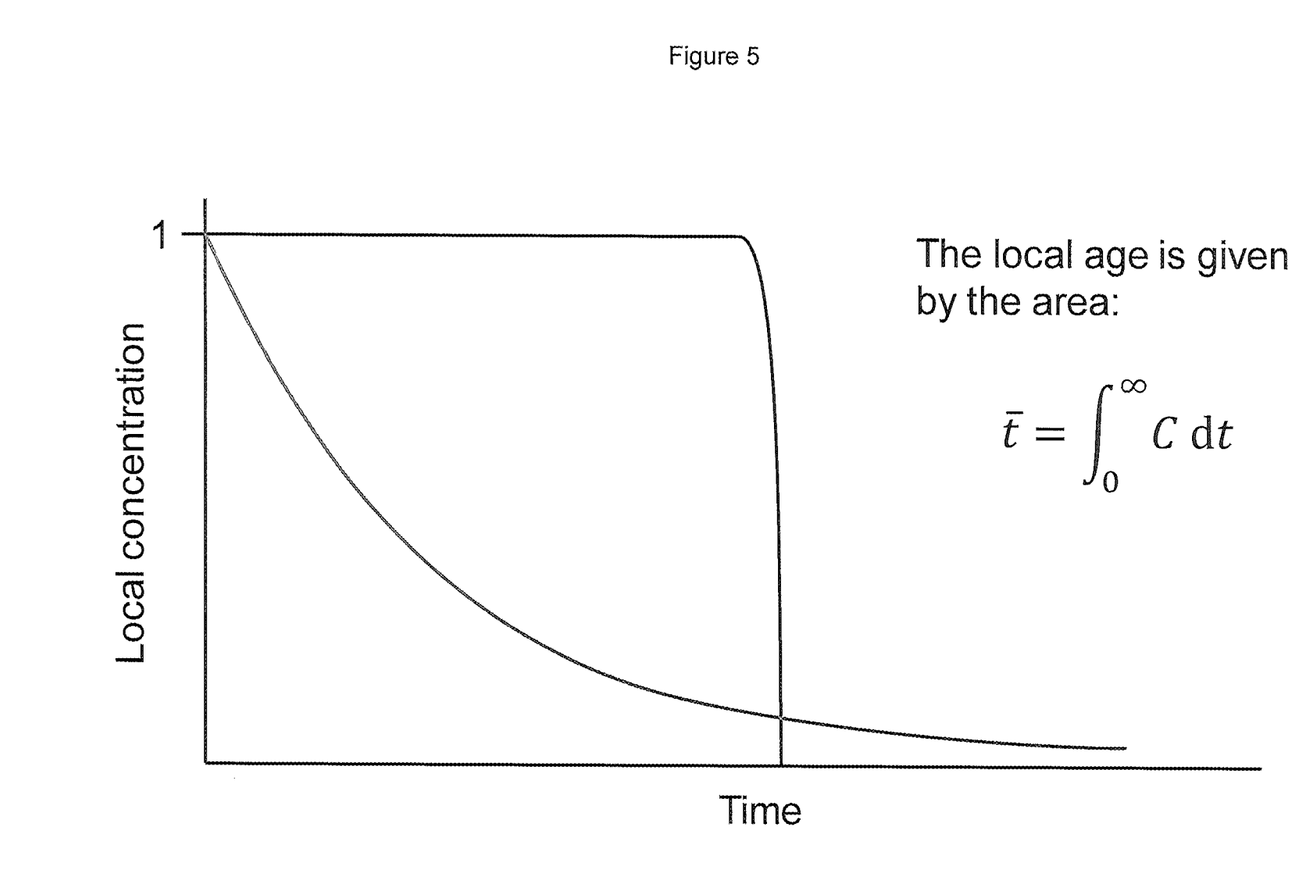
FIG. 5 shows the integral that defines the local age in a pixel.
Figure 6:
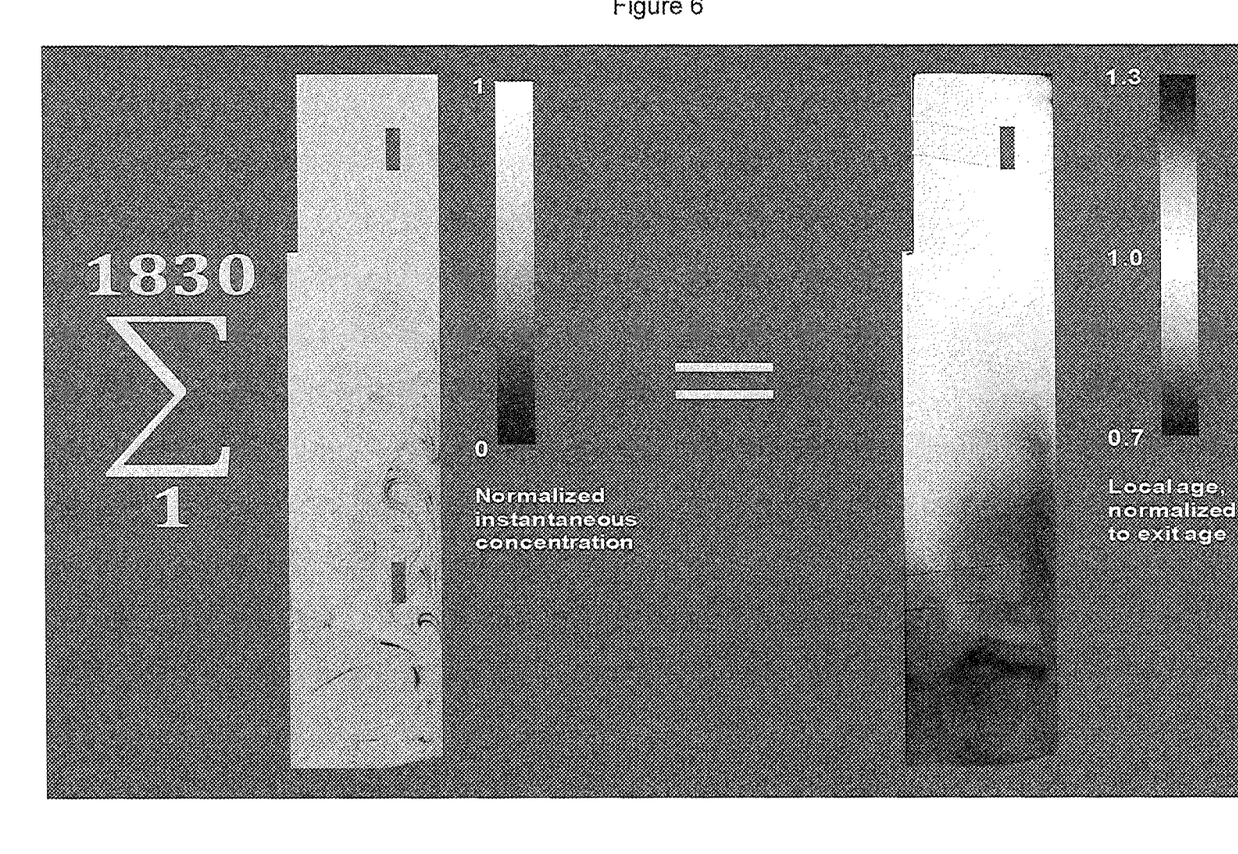
FIG. 6 shows the same integral approximated as a sum of instantaneous concentrations, and the resulting local age distribution for one experiment.

This normalization procerducer corrects for variations in the laser plane intensity, the camera pixels, and the transmitting optics. Additional corrections may be required correct for the effects of laser attenuation by the dye. The result is a series of images showing the normalized dye concentration in each frame. These images can then be integrated over time to calculate the local age distribution of the fluid in the reactor (this is shown in FIGS. 5 and 6). The local fluid ages, normalized to the exit age, may be between 0.5 and 1.3, preferably from 0.8 to 1.0.

From the data it is also possible to calculate the coefficient of variance (CoV), which is the standard deviation of the local fluid ages in the reactor divided by the mean of the local fluid ages in the reactor.

In some embodiments, the local age of the reactor contents normalized to the exit age is from 0.5 to 1.3; in some embodiments the local age of the reactor contents normalized to the exit age is from 0.6 to 1.2; in other embodiments the local age of the reactor contents normalized to the exit age is from 0.8 to 1.0. The closer this ratio of normalized age is to 1 the better mixed the reactor is. Additionally, the coefficient of variance (CoV), which is the standard deviation of the normalized hold up time in the reactor divided by the mean normalized average age of the fluid in the reactor (a unitless number), should typically be low, in some embodiments between 0.01 to 0.10, and in further embodiments from 0.01 to 0.06.

In a further embodiment there is provided a method to determine a preferred inlet location for a continuous stirred tank reactor (CSTR) comprising:

1) preparing a transparent model comparable (scaleable) to the reactor in question, including the agitator design and a number of alternate inlet ports, preferably having at least one planar exterior surface;

2) filling the reactor with a test fluid having a viscosity chosen to produce the desired Reynolds number, which fluid contains a uniform concentration of a tracer dye which fluoresces under a known wavelength of incident light;

3) flowing six times the reactor volume of test fluid without dye into and through the reactor using a selected inlet port with the agitator running at a constant speed to provide a constant Reynolds number to introduce a step change in concentration of the tracer dye in the reactor;

4) while the dye is being washed out of the reactor and during mixing, subjecting the reactor contents to a plane of laser light (through the planar surface of the reactor), whose wavelength causes the dye to fluoresce at a different wavelength from that of the laser;

5) taking digital images of the fluorescent light from the reactor through a filter to filter out the incident laser light at a rate synchronized with the rate of rotation of the impeller so that the blades are synchronized in all images;

6) calculating the normalized dye concentration in each pixel of each image;

7) integrating the normalized concentration in each pixel over all images in time to calculate the average local fluid age of each pixel;

8) calculating the standard deviation and the mean of the local ages and the coefficient of variation and storing the results;

9) iteratively repeating steps 1 through 8 for different inlets to the reactor;

10) comparing the stored data to determine the inlet which provides one, preferably two, or more of:
  i) a normalized dye concentration (normalized age of the rector contents) from 0.5 to 1.3;
  ii) a coefficient of variance from 0.01 to 0.1; and
  iii) a minimum standard deviation in the average age of the reactor contents, and 11) selecting the input port which provides the optimum values from step 8.

In a further embodiment there is provided a method to determine a preferred agitator for a continuous stirred tank reactor (CSTR) reactor comprising:

1) preparing a transparent model comparable (scalable) to the reactor in question, including the agitator design and a number of alternate inlet ports preferably having at least one planar exterior surface;

2) filling the reactor with a test fluid having a viscosity chosen to produce the desired Reynolds number, which fluid contains a uniform concentration of a tracer dye which fluoresces under a known wavelength of incident light;

3) flowing six timer the reactor volume of test fluid without dye into and through the reactor using a selected inlet port with the agitator running at a constant speed to provide a constant Reynolds number to introduce a step change in concentration of the tracer dye in the reactor;

4) while the dye is being washed out of the reactor and during mixing, subjecting the reactor contents to a plane of laser light (through the planar surface of the reactor), whose wavelength causes the dye to fluoresce at a different wavelength from that of the laser;

5) taking digital images of the fluorescent light from the reactor through a filter to filter out the incident laser light at a rate synchronized with the rate of rotation of the impeller so that the blades are synchronized in all images;

6) calculating the normalized dye concentration in each pixel of each image;

7) integrating the normalized concentration in each pixel over all images in time to calculate the average local fluid age of each pixel;

8) calculating the standard deviation and the mean of the local ages and the coefficient of variation and storing the results;

9) iteratively repeating steps 1 through 8 for different agitators for the reactor;

10) comparing the stored data to determine the agitator which provides one, preferably two, or more of:
  i) a normalized dye concentration (normalized age of the rector contents) from 0.5 to 1.3;
  ii) a coefficient of variance from 0.01 to 0.1; and
  iii) a minimum standard deviation in the average age of the reactor contents, and 11) selecting the agitator which provides the optimum values from step 8.

Having determined the preferred inlet port and agitator, one may repeat the above to determine the preferred flow rate into the reactor and the preferred agitator speed.

In a further embodiment there is a method to determine a preferred agitator speed for a continuous stirred tank reactor (CSTR) reactor comprising:

1) preparing a transparent model comparable (scalable) to the reactor in question including the agitator design and a number of alternate inlet ports preferably having at least one planar exterior surface;

2) filling the reactor with a test fluid having a viscosity chosen to produce the desired Reynolds number, which fluid contains a uniform concentration of a tracer dye which fluoresces under a known wavelength of incident light;

3) flowing six times the reactor volume of test fluid without dye into and through the reactor at a constant flow rate using a selected feed port and agitator running at a constant speed to provide a constant Reynolds number to introduce a step change in concentration of the tracer dye in the reactor;

4) while the dye is being washed out of the reactor and during mixing, subjecting the reactor contents to a plane of laser light (through the planar surface of the reactor), whose wavelength causes the dye to fluoresce at a different wavelength from that of the laser;

5) taking digital images of the fluorescent light from the reactor through a filter to filter out the incident laser light at a rate synchronized with the rate of rotation of the impeller so that the blades are synchronized in all images;

6) calculating the normalized dye concentration in each pixel of each image;

7) integrating the normalized concentration in each pixel over all images in time to calculate the average local fluid age of each pixel;

8) calculating the standard deviation and the mean of the local ages and the coefficient of variation and storing the results;

9) iteratively repeating steps 1 through 8 for different agitator speeds;

10) comparing the stored data to determine the inlet which provides one, preferably two, or more of:
  i) a normalized dye concentration (normalized age of the rector contents) from 0.5 to 1.3;
  ii) a coefficient of variance from 0.01 to 0.1; and
  iii) a minimum standard deviation in the average age of the reactor contents, and 11) selecting the agitator speed which provides the optimum values from step 8.

In a further embodiment there is provided a method a method to determine a preferred feed flow rate to a continuous stirred tank reactor (CSTR) reactor comprising:

1) preparing a transparent model comparable (scalable) to the reactor in question, including the agitator design and a number of alternate inlet ports preferably having at least one planar exterior surface;

2) filling the reactor with a test fluid having a viscosity chosen to produce the desired Reynolds number, which fluid contains a uniform concentration of a tracer dye which fluoresces under a known wavelength of incident light;

3) flowing six times the reactor volume of test fluid without dye into and through the reactor at a constant flow rate using a selected feed port and agitator running at a constant speed to provide a constant Reynolds number to introduce a step change in concentration of the tracer dye in the reactor;

4) while the dye is being washed out of the reactor and during mixing, subjecting the reactor contents to a plane of laser light (through the planar surface of the reactor), whose wavelength causes the dye to fluoresce at a different wavelength from that of the laser;

5) taking digital images of the fluorescent light from the reactor through a filter to filter out the incident laser light at a rate synchronized with the rate of rotation of the impeller so that the blades are synchronized in all images;

6) calculating the normalized dye concentration in each pixel of each image;

7) integrating the normalized concentration in each pixel over all images in time to calculate the average local fluid age of each pixel;

8) calculating the standard deviation and the mean of the local ages and the coefficient of variation and storing the results;

9) iteratively repeating steps 1 through 8 for different feed flow rates to the reactor;

10) comparing the stored data to determine the feed flow rate which provides one, preferably two, or more of:
   i) a normalized dye concentration (normalized age of the rector contents) from 0.5 to 1.3;
   ii) a coefficient of variance from 0.01 to 0.1; and
   iii) a minimum standard deviation in the average age of the reactor contents, and 11) selecting the reactor feed rate which provides the optimum values from step 8.

The foregoing values and ratios are then applied in the operation of the reactor to improve product quality and consistency.

The foregoing process may be applied to a number of chemical reactions, particularly the bulk or solution polymerization of polystyrene and high impact polystyrene ("HIPS") and the polymerization of one or more $C_{2-8}$ alpha olefins such of ethylene, propylene, 1-butene, 1-hexene, and 1-octene.

Generally the polymerizations of olefins may take place in a solution in which the solvent is selected from the group consisting of one or more $C_{5-12}$ saturated hydrocarbons, typically a $C_{3-8}$ hydrocarbon, which may be unsubstituted or substituted by a $C_{1-4}$ alkyl group, such as pentane, methyl pentane, hexane, heptane, octane, cyclohexane, methylcyclohexane and hydrogenated naphtha. An example of a suitable solvent that is commercially available is "Isopar E" ($C_{8-12}$ aliphatic solvent, Exxon Chemical Co.).

The reaction may take place in one or more reactors in parallel or in series. The calculations in accordance with the present invention would be applied to each reactor used in the process.

Typically, solution polymerization processes are conducted at temperatures from 130° C. to 300° C., in some embodiments from 120° C. to 250° C. in some embodiments from 180° C. to 220° C. and pressures from 5 to 40 MPa, in some embodiments from 14 to 22 MPa.

The pressure in the reactor system should be high enough to maintain the polymerization solution as a single phase solution and to provide the necessary upstream pressure to feed the polymer solution from the reactor system through a heat exchanger system and to a devolatilization system.

The solution polymerization process may be conducted in a stirred "reactor system" or an equivalent (i.e. a loop reactor) (CSTR) comprising one or more stirred tank reactors or in a mixed loop and stirred tank reactor system. The CSTR reactors may be cylindrical or spherical. The agitator may be selected from the group consisting of auger agitators, anchor agitators, radial blade turbine, pitched blade turbine, hydrofoil impeller, or a hybrid impeller comprising one or more of these elements. The reactors may be in tandem or parallel operation. In a dual tandem reactor system, the first polymerization reactor preferably operates at lower temperature. The residence time in each reactor will depend on the design and the capacity of the reactor and the integrated operation process. Generally, the reactors should be operated under conditions to achieve a thorough mixing of the reactants. In addition, it is preferred that from 20 to 60 wt % of the final polymer is polymerized in the first reactor, with the balance being polymerized in the second reactor.

It is highly desirable that the CSTRs be operated in a nearly homogeneous manner, which may be ascertained by the local ages within the reactor being nearly equal to the exit age, or by having a very small coefficient of variance (CoV) of local ages, for example in some embodiments between 0.01 to 0.10, in further embodiments from 0.01 to 0.06.

The above unitless values may be used to compare (rank) different reactors (producing the same product) at the same or different sites. This may lead to a better implementation of process procedures used in different reactor such as from a pilot plant to a commercial plant. Additionally, the technique may be used to compare mixing with different agitators.

In the solution polymerization of alpha olefins a number of catalysts may be used alone or in combination. The catalysts may be selected from the group consisting of single site catalysts, Ziegler-Natta catalysts, and chrome catalysts. In solution polymerization process the catalysts are not supported. They may be formed in situ in line(s) leading to the reactor (i.e. online) or could be pre-formed off line. The off-line catalysts need to be soluble or dispersable in the solvent for the reaction or a solvent which will not interfere with the reaction.

Chrome Catalysts

The chromium compound used can be any appropriate chromium salt or an inorganic or organic chromium compound. For example, chromocene (i.e. bis(cyclopentadienyl) chromium), silyl chromate and chromium oxide may be used. Preferably, the chromium compound is a chromium oxide or a silyl chromate compound.

The chromium oxide may be $CrO_3$ or any compound that is convertible to $CrO_3$ under oxidizing conditions. Examples of compounds that are convertible to $CrO_3$ under oxidizing conditions are disclosed in U.S. Pat. Nos. 2,825,721; 3,023,203; 3,622,251; and 4,011,382 and include but are not limited to chromic acetyl acetone, chromic chloride, chromic nitrate, chromic acetate, chromic sulfate, ammonium chromate, ammonium dichromate and other soluble salts of chromate.

The silyl chromate (i.e. silyl chromium) catalysts will have at least one group of the formula I:

wherein R is a hydrocarbyl group having from 1 to 14 carbon atoms.

In a preferred aspect of the invention, the silyl chromate catalyst is a bis-trihydrocarbylsilylchromate having the formula II:

wherein R' is a hydrocarbyl group having from 1 to 14 carbon atoms. R' can independently be any type of hydrocarbyl group such as an alkyl, alkaryl, aralkyl or an aryl radical. Some non-limiting examples include methyl, ethyl, propyl, iso-propyl, n-butyl, iso-butyl, n-pentyl, iso-pentyl, t-pentyl, hexyl, 2-methyl-pentyl, heptyl, octyl, 2-ethylhexyl, nonyl, decyl, hendecyl, dodecyl, tridecyl, tetradecyl, benzyl, phenethyl, p-methyl-benzyl, phenyl, tolyl, xylyl, naphthyl, ethylphenyl, methylnaphthyl, dimethylnaphthyl, and the like. Illustrative of the preferred silylchromates but by no means exhaustive or complete of those that can be employed in this process are such compounds as bis-trimethylsilylchromate, bis-triethylsilylchromate, bis-tributylsilylchromate, bis-triisopentylsilylchromate, bis-tri-2-ethylhexylsilylchromate, bis-tridecylsilylchromate, bis-tri(tetradecyl) silylchromate, bis-tribenzylsilylchromate, bis-triphenethylsilylchromate, bis-triphenylsilylchronnate, bis-tritolylsilylchromate, bis-trixylylsilylchromate, bis-trinaphthylsilylchromate, bis-triethylphenylsilylchromate, bis-trimethylnaphthylsilylchromate, polydiphenylsilylchromate, polydiethylsilylchromate and the like. Examples of bis-trihydrocarbylsilylchromate catalysts are also disclosed in U.S. Pat. Nos. 3,704,287 and 4,100,105.

Ziegler-Natta Catalysts

Typically, the Ziegler-Natta catalysts comprise, a magnesium compound (optionally in the presence of a halide donor to precipitate magnesium halide), a titanium compound and an aluminum compound, in the presence of an electron donor. The aluminum compound may be added at several stages.

Typically the Ziegler-Natta catalyst useful in accordance with the present invention will comprise an aluminum compound of the formula $R^1{}_bAl(OR^1)_aX_{3-(a+b)}$ wherein a is an integer from 0 to 3, b is an integer from 0 to 3 and the sum of a+b is from 0 to 3, $R^1$ is the same or different $C_{1-10}$ alkyl radical and X is a chlorine atom, a transition metal, preferably a titanium compound of the formula $Ti((O)_cR^2)_dX_e$ wherein $R^2$ is selected from the group consisting of $C_{1-4}$ alkyl radicals, $C_{6-10}$ aromatic radicals and mixtures thereof, X is selected from the group consisting of a chlorine atom and a bromine atom, c is 0 or 1, d is 0 or an integer up to 4 and e is 0 or an integer up to 4 and the sum of d+e is the valence of the Ti atom; a magnesium compound of the formula $(R^5)_fMg\,X_{2-f}$ wherein each $R^5$ is independently a $C_{1-8}$ alkyl radical and f is 0, 1 or 2; $CCl_4$ or an alkyl halide selected from the group consisting of $C_{3-6}$ secondary or tertiary alkyl halides and optionally an electron donor, a molar ratio of total Al to Ti (e.g. the first and/or second aluminum additions (if two additions are made) $Al^1$ and $Al^2$ from 2:1 to 15:1 a molar ratio of Al from the second aluminum ($Al^2$) addition to Ti from 1:1 to 8:1; a molar ratio of Mg:Ti from 0.5:1 to 20:1, preferably 1:1 to 12:1; a molar ratio of active halide (this excludes the halide from the Al and Ti compounds) from the $CCl_4$ or alkyl halide to Mg from 1:1 to 6:1, preferably 1.5:1 to 5:1; and a molar ratio of electron donor to Ti from 0:1 to 18:1, preferably from 1:1 to 15:1.

Typically, the catalyst components are reacted in an organic medium such as an inert 05-10 hydrocarbon which may be unsubstituted or is substituted by a $C_{1-4}$ alkyl radical. Some solvents include pentane, iso-pentane, hexane, iso-hexane, heptane, octane, cyclohexane, methyl cyclohexane, hydrogenated naphtha and ISOPAR®E (a solvent available from Exxon Chemical Company) and mixtures thereof.

Typically, the aluminum compounds useful in the formation of the catalyst or catalyst precursor in accordance with the present invention have the formula $R^1{}_bAl(OR^1)_aX_{3-(a+b)}$ wherein a is an integer from 0 to 3, b is an integer from 0 to 3 and the sum of a+b is from 0 to 3, $R^1$ is the same or different $C_{1-10}$ alkyl radical and X is a chlorine atom. Suitable aluminum compounds include, trimethyl aluminum (TMA), triethyl aluminum (TEAL), isoprenyl aluminum, tri-isobutyl aluminum (TiBAL), diethyl aluminum chloride (DEAC), tri-n-hexyl aluminum (TnHAl), tri-n-octyl aluminum (TnOAl), diethyl aluminum ethoxide and mixtures thereof. The aluminum compounds containing a halide may be an aluminum sesqui-halide. Preferably, in the aluminum compound a is 0, b is 3 and $R^1$ is a $C_{1-8}$ alkyl radical.

The magnesium compound may be a compound of the formula $(R^5)_fMgX_{2-f}$ wherein each $R^5$ is independently selected from the group consisting of $C_{1-8}$ alkyl radicals and f is 0, 1 or 2. Some commercially available magnesium compounds include magnesium chloride, butyl octyl magnesium, dibutyl magnesium and butyl ethyl magnesium. If the magnesium compound is soluble in the organic solvent it may be used in conjunction with a halogenating agent or reactive organic halide to form magnesium halide (i.e. $MgX_2$ where X is a halogen preferably chlorine or bromine, most preferably chlorine), which precipitates from the solution (potentially forming a substrate for the Ti compound). Some halogenating agents include $CCl_4$ or a secondary or tertiary halide of the formula $R^6Cl$ wherein $R^6$ is selected from the group consisting of secondary and tertiary $C_{3-6}$ alkyl radicals. Suitable chlorides include sec-butyl chloride, t-butyl chloride and sec-propyl chloride. The reactive halide is added to the catalyst in a quantity such that the active Cl:Mg molar ratio should be from 1.5:1 to 5:1, preferably from 1.75:1 to 4:1, most preferably from 1.9:1 to 3.5:1.

The titanium compound in the catalyst may have the formula $Ti((O)_cR^2)_dX_e$ wherein $R^2$ is selected from the group consisting of $C_{1-4}$ alkyl radicals, $C_{6-10}$ aromatic radicals and mixtures thereof, X is selected from the group consisting of a chlorine atom and a bromine atom, c is 0 or 1, d is 0 or an integer up to 4 and e0 or an integer up to 4 and the sum of d+e is the valence of the Ti atom. If c is 1 the formula becomes $Ti(OR^2)_dX_e$ wherein. $R^2$ is selected from the group consisting of $C_{1-4}$ alkyl radicals, and $C_{6-10}$ aromatic radicals, X is selected from the group consisting of a chlorine atom and a bromine atom, preferably a chlorine atom, d is 0 or an integer up to 4 and e is 0 or an integer up to 4 and the sum of d+e is the valence of the Ti atom. The titanium compound may be selected from the group consisting of $TiCl_3$, $TiCl_4$, $Ti(OC_4H_9)_4$, $Ti(OC_3H_7)_4$, and $Ti(OC_4H_9)Cl_3$ and mixtures thereof. Most preferably the titanium compound is selected from the group consisting of $Ti(OC_4H_9)_4$ and $TiCl_4$ and mixtures thereof.

As noted above, an electron donor may be, and in fact is preferably used in the catalysts or catalysts precursor used in accordance with the present invention. The electron donor may be selected from the group consisting of $C_{3-18}$ linear or cyclic aliphatic or aromatic ethers, ketones, esters, aldehydes, amides, nitriles, amines, phosphines or siloxanes. Preferably, the electron donor is selected from the group consisting of diethyl ether, triethyl amine, 1,4-dioxane, tetrahydrofuran, acetone, ethyl acetate, and cyclohexanone and mixtures thereof. The electron donor may be used in a molar ratio to the titanium from 0:1 to 18:1 preferably in a molar ratio to Ti from 3:1 to 15:1, most preferably from 3:1 to 12:1.

In the catalyst or catalyst precursor the molar ratio of Mg:Ti may be from 0.5:1 to 20:1, preferably from 1:1 to 12:1, most preferably from 1:1 to 10:1. If a second aluminum addition is used the molar ratio of second aluminum ($Al^2$) to titanium in the catalyst may be from 1:1 to 8:1, preferably from 1.5:1 to 7:1, most preferably from 2:1 to 6:1. Generally, from 0 to not more than about 60 weight %, preferably from 10 to 50 weight %, of the aluminum (compound in the catalyst) may be used to treat the support (e.g. Al). The molar ratio of active halide (from the alkyl halide or $CCl_4$) to Mg may be from 1.5:1 to 5:1 preferably from 1.75:1 to 4:1, most preferably from 1.9:1 to 3.5:1. The molar ratio of electron donor, if present, to Ti may be from 1:1 to 15:1, most preferably from 3:1 to 12:1.

The Ziegler-Natta catalyst may be activated with one or more co-catalysts of the formula $Al(R^7)_{3-g}X_g$ wherein $R^7$ is a $C_{1-6}$ alkyl radical, X is a chlorine atom and g is 0 or 1 and mixtures thereof. The co-catalyst may be selected from the group consisting of tri $C_{1-6}$ alkyl aluminums, alkyl aluminum chlorides (e.g. di $C_{1-6}$ alkyl aluminum chloride), and mixtures thereof. This includes, but is not limited to, trimethyl aluminum, triethyl aluminum, tri propyl aluminum, tributyl aluminum, tri isobutyl aluminum, isoprenylaluminum, n-hexyl aluminum, diethyl aluminum chloride, dibutyl aluminum chloride, and mixtures thereof. A preferred co-catalyst is triethyl aluminum.

The co-catalyst may be fed to the reactor to provide from 10 to 130, preferably 10 to 80 more preferably from 15 to 70, most preferably from 20 to 60 ppm of aluminum (Al ppm) based on the polymer production rate.

Single-Site Catalysts

The present invention may use a catalyst which is a bulky ligand single site catalyst.

The bulky ligand single site catalysts may have the formula:

$$(L)_n\text{-M-}(Y)_p$$

wherein M is selected from the group consisting of Ti, Zr and Hf; L is a monoanionic ligand independently selected from the group consisting of cyclopentadienyl-type ligands, and a bulky heteroatom ligand containing not less than five atoms in total (typically of which at least 20%, preferably at least 25% numerically are carbon atoms) and further containing at least one heteroatom selected from the group consisting of boron, nitrogen, oxygen, phosphorus, sulfur and silicon, said bulky heteroatom ligand being sigma or pi-bonded to M, Y is independently selected from the group consisting of activatable ligands; n may be from 1 to 3; and p may be from 1 to 3, provided that the sum of n+p equals the valence state of M, and further provided that two L ligands may be bridged for example by a silyl radical or a $C_{1-4}$ alkyl radical, or a mixture thereof.

The term "cyclopentadienyl" refers to a 5-member carbon ring having delocalized bonding within the ring and typically being bound to the active catalyst site, generally a group 4 metal (M) through $\eta^5$-bonds. The cyclopentadienyl ligand may be unsubstituted or up to fully substituted with one or more substituents independently selected from the group consisting of $C_{1-10}$ hydrocarbyl radicals which hydrocarbyl substituents are unsubstituted or further substituted by one or more substituents independently selected from the group consisting of a halogen atom and a $C_{1-4}$ alkyl radical; a halogen atom; a $C_{1-8}$ alkoxy radical; a $C_{6-10}$ aryl or aryloxy radical; an amido radical which is unsubstituted or substituted by up to two $C_{1-8}$ alkyl radicals; a phosphido radical which is unsubstituted or substituted by up to two $C_{1-8}$ alkyl radicals; silyl radicals of the formula —Si—$(R)_3$ wherein each R is independently selected from the group consisting of hydrogen, a $C_{1-8}$ alkyl or alkoxy radical, and $C_{6-10}$ aryl or aryloxy radicals; and germanyl radicals of the formula Ge—$(R)_3$ wherein R is as defined above.

Typically, the cyclopentadienyl-type ligand is selected from the group consisting of a cyclopentadienyl radical, an indenyl radical and a fluorenyl radical which radicals are unsubstituted or up to fully substituted by one or more substituents independently selected from the group consisting of a fluorine atom, a chlorine atom; $C_{1-4}$ alkyl radicals; and a phenyl or benzyl radical which is unsubstituted or substituted by one or more fluorine atoms.

In the formula above, if none of the L ligands is bulky heteroatom ligand, then the catalyst could be a mono cyclopentadienyl (Cp) catalyst, a bridged or unbridged bis Cp catalyst or a bridged constrained geometry type catalysts or a tris Cp catalyst.

If the catalyst contains one or more bulky heteroatom ligands, the catalyst would have the formula:

wherein M is a transition metal selected from the group consisting of Ti, Hf and Zr; C is a bulky heteroatom ligand preferably independently selected from the group consisting of phosphinimine ligands (as described below) and ketimide ligands (as described below); L is a monoanionic ligand independently selected from the group consisting of cyclopentadienyl-type ligands; Y is independently selected from the group consisting of activatable ligands; m is 1 or 2; n is 0 or 1; and p is an integer and the sum of m+n+p equals the valence state of M, provided that when m is 2, C may be the same or different bulky heteroatom ligands.

For example, the catalyst may be a bis (phosphinimine), a bis (ketimide), or a mixed phosphinimine ketimide dichloride complex of titanium, zirconium or hafnium. Alternately, the catalyst could contain one phosphinimine ligand or one ketimide ligand, one "L" ligand (which is most preferably a cyclopentadienyl-type ligand) and two "Y" ligands (which are preferably both chloride).

The preferred metals (M) are from Group 4 (especially titanium, hafnium or zirconium) with titanium being most preferred. In one embodiment, the catalysts are group 4 metal complexes in the highest oxidation state.

The catalyst may contain one or two phosphinimine ligands (PI) which are bonded to the metal. The phosphinimine ligand is defined by the formula:

wherein each $R^{21}$ is independently selected from the group consisting of a hydrogen atom; a halogen atom; $C_{1-20}$, preferably $C_{1-10}$ hydrocarbyl radicals which are unsubstituted by or further substituted by a halogen atom; a $C_{1-8}$ alkoxy radical; a $C_{6-10}$ aryl or aryloxy radical; an amido radical; a silyl radical of the formula:

—Si—$(R^{22})_3$ wherein each $R^{22}$ is independently selected from the group consisting of hydrogen, a $C_{1-8}$ alkyl or alkoxy radical, and $C_{6-10}$ aryl or aryloxy radicals; and a germanyl radical of the formula:

—Ge—$(R^{22})_3$ wherein $R^{22}$ is as defined above.

The preferred phosphinimines are those in which each $R^{21}$ is a hydrocarbyl radical, preferably a $C_{1-6}$ hydrocarbyl radical, such as a t-butyl radical.

Suitable phosphinimine catalysts are Group 4 organometallic complexes which contain one phosphinimine ligand (as described above) and one ligand L which is either a cyclopentadienyl-type ligand or a heteroatom ligand.

As used herein, the term "ketimide ligand" refers to a ligand which:

(a) is bonded to the transition metal via a metal-nitrogen atom bond;

(b) has a single substituent on the nitrogen atom (where this single substituent is a carbon atom which is doubly bonded to the N atom); and (c) has two substituents Sub 1 and Sub 2 (described below) which are bonded to the carbon atom.

Conditions a, b and c are illustrated below:

The substituents "Sub 1" and "Sub 2" may be the same or different. Exemplary substituents include hydrocarbyls having from 1 to 20, preferably from 3 to 6, carbon atoms, silyl groups (as described below), amido groups (as described below) and phosphido groups (as described below). For reasons of cost and convenience, it is preferred that these substituents both be hydrocarbyls, especially simple alkyls radicals and most preferably tertiary butyl radicals.

Suitable ketimide catalysts are Group 4 organometallic complexes which contain one ketimide ligand (as described above) and one ligand L which is either a cyclopentadienyl-type ligand or a heteroatom ligand.

The term bulky heteroatom ligand is not limited to phosphinimine or ketimide ligands and includes ligands which contain at least one heteroatom selected from the group consisting of boron, nitrogen, oxygen, phosphorus, sulfur or silicon. The heteroatom ligand may be sigma or pi-bonded to the metal. Exemplary heteroatom ligands include silicon-containing heteroatom ligands, amido ligands, alkoxy ligands, boron heterocyclic ligands and phosphole ligands, as all described below.

Silicon containing heteroatom ligands are defined by the formula:

wherein the — denotes a bond to the transition metal and Y is sulfur or oxygen.

The substituents on the Si atom, namely $R_x$, $R_y$ and $R_z$, are required in order to satisfy the bonding orbital of the Si atom. The use of any particular substituent $R_x$, $R_y$ or $R_z$ is not especially important to the success of this invention. It is preferred that each of $R_x$, $R_y$ and $R_z$ is a $C_{1-2}$ hydrocarbyl group (i.e. methyl or ethyl) simply because such materials are readily synthesized from commercially available materials.

The term "amido" is meant to convey its broad, conventional meaning. Thus, these ligands are characterized by (a) a metal-nitrogen bond; and (b) the presence of two substituents (which are typically simple alkyl or silyl groups) on the nitrogen atom.

The terms "alkoxy" and "aryloxy" is intended to convey its conventional meaning. Thus, these ligands are characterized by (a) a metal oxygen bond; and (b) the presence of a hydrocarbyl group bonded to the oxygen atom. The hydrocarbyl group may be a $C_{1-10}$ straight chained, branched or cyclic alkyl radical or a $C_{6-13}$ aromatic radical which radicals are unsubstituted or further substituted by one or more $C_{1-4}$ alkyl radicals (e.g. 2,6 di-tertiary butyl phenoxy).

Boron heterocyclic ligands are characterized by the presence of a boron atom in a closed ring ligand. This definition includes heterocyclic ligands which may also contain a nitrogen atom in the ring. These ligands are well known to those skilled in the art of olefin polymerization and are fully described in the literature (see, for example, U.S. Pat. Nos. 5,637,659; 5,554,775; and the references cited therein).

The term "phosphole" is also meant to convey its conventional meaning. "Phospholes" are cyclic dienyl structures having four carbon atoms and one phosphorus atom in the closed ring. The simplest phosphole is $C_4PH_4$ (which is analogous to cyclopentadiene with one carbon in the ring being replaced by phosphorus). The phosphole ligands may be substituted with, for example, $C_{1-20}$ hydrocarbyl radicals (which may, optionally, contain halogen substituents); phosphido radicals; amido radicals; or silyl or alkoxy radicals. Phosphole ligands are also well known to those skilled in the art of olefin polymerization and are described as such in U.S. Pat. No. 5,434,116 (Sone, to Tosoh).

The term "activatable ligand" (i.e. "Y" in the above formula) or "leaving ligand" refers to a ligand which may be activated by the aluminoxane (also referred to as an "activator") to facilitate olefin polymerization. Exemplary activatable ligands are independently selected from the group consisting of a hydrogen atom; a halogen atom, preferably a chlorine or fluorine atom; a $C_{1-10}$ hydrocarbyl radical, preferably a $C_{1-4}$ alkyl radical; a $C_{1-10}$ alkoxy radical, preferably a $C_{1-4}$ alkoxy radical; and a $C_{5-10}$ aryl oxide radical; each of which said hydrocarbyl, alkoxy, and aryl oxide radicals may be unsubstituted by or further substituted by one or more substituents selected from the group consisting of a halogen atom, preferably a chlorine or fluorine atom; a $C_{1-8}$ alkyl radical, preferably a $C_{1-4}$ alkyl radical; a $C_{1-8}$ alkoxy radical, preferably a $C_{1-4}$ alkoxy radical; a $C_{6-10}$ aryl or aryloxy radical; an amido radical which is unsubstituted or substituted by up to two $C_{1-8}$, preferably $C_{1-4}$ alkyl radicals; and a phosphido radical which is unsubstituted or substituted by up to two $C_{1-8}$, preferably $C_{1-4}$ alkyl radicals.

The number of activatable ligands (Y) depends upon the valence of the metal and the valence of the activatable ligand. The preferred catalyst metals are Group 4 metals in their highest oxidation state (i.e. 4$^+$) and the preferred activatable ligands are monoanionic (such as a halide—especially chloride or $C_{1-4}$ alkyl radicals, especially methyl radicals.

In one embodiment of the present invention, the transition metal complex may have the formula: $[(Cp)_nM[N=P(R^{21})]_mY_p$ wherein M is the transition (group 4) metal; Cp is a $C_{5-13}$ ligand containing a 5-membered carbon ring having delocalized bonding within the ring and bound to the metal atom through covalent $\eta^5$ bonds and said ligand being unsubstituted or up to fully 4 substituted with one or more substituents selected from the group consisting of a halogen atom, preferably chlorine or fluorine; $C_{1-4}$ alkyl radicals; and benzyl and phenyl radicals which are unsubstituted or substituted by one or more halogen atoms, preferably fluorine; $R^{21}$ is a substituent selected from the group consisting of $C_{1-6}$ straight chained or branched alkyl radicals, $C_{6-10}$ aryl and aryloxy radicals which are unsubstituted or may be substituted by up to three $C_{1-4}$ alkyl radicals, and silyl radicals of the formula $-Si-(R)_3$ wherein R is $C_{1-4}$ alkyl radical or a phenyl radical; Y is selected from the group consisting of a leaving ligand; n is 1 or 2; m is 1 or 2; and the valence of the transition metal$-(n+m)=p$.

For the single site type catalyst, the activator may be a complex aluminum compound of the formula $R^{12}{}_2AlO$ $(R^{12}AlO)_q AlR^{12}{}_2$ wherein each $R^{12}$ is independently selected from the group consisting of $C_{1-20}$ hydrocarbyl radicals and q is from 3 to 50.

In the aluminum compound preferably, $R^{12}$ is a methyl radical and q is from 10 to 40.

The catalysts systems in accordance with the present invention may have a molar ratio of aluminum from the aluminoxane to transition metal from 5:1 to 1000:1, preferably from 10:1 to 500:1, most preferably from 30:1 to 300:1, most desirably from 50:1 to 120:1.

The phrase "and mixtures thereof" in relation to the catalyst mean the catalyst may be a mixture of one or more chromium catalysts, a mixture of one or more Ziegler-Natta catalysts, a mixture of one or more bulky ligand single site catalysts, a mixture of one or more chromium catalysts with one or more Ziegler Natta catalysts, a mixture of one or more Ziegler-Natta catalysts with one or more bulky ligand single site catalysts and a mixture of one or more chromium catalysts with one or more bulky ligand single site catalysts.

The preparation of clear scalable model of the reactor in question including the agitator may be done in a number of manners. Typically, the "reactor" is modeled from a clear tough transparent plastic such as a polycarbonate or an acrylic polymer. Such a model may exist for example in a laboratory and has been used for experimental purposes relating to the operation of a plant or pilot plant reactor. Dimensionless numbers have already been developed for scaling the model reactor to for example a plant or a pilot plant. Then the reactor can be used under conditions which reflect plant operation in the experiments.

The model may be prepared form blueprints for the reactor an appropriately scaled. Then the model could be machined from the plastic or in some cases the model could be a 3D printing based on the reactor design. The agitator need not be transparent. It is important that the model be scalable from a fluid dynamics point of view such as Reynolds numbers and flow rates. This may involve selecting an appropriate fluid to use during the operation of the model.

For the operation of the model it may be desirable to use variable speed drives for the agitator and the pumps to be able to model the reactor and model variations in its operation.

Example

The present invention will now be illustrated by the following non-limiting example.

The apparatus consists of

1. A transparent acrylic reactor body that has a 4-inch cylindrical interior and a square exterior. The square exterior minimizes the refractive distortion of the images. The reactor height is 2.14 times the inside diameter, and the reactor has a bottom inlet on the centreline, another inlet in the side wall, and an outlet in the upper head.

2. A MaxBlend impeller designed for this unusually tall tank. (MaxBlend impellers are normally installed in tanks with aspect ratios from 1 to 1.5).

3. A test fluid of 74% glycerol in water, giving it a viscosity of about 0.03 Pa·s. Half of this fluid was dyed with 0.25 mg/L sodium fluorescein.

4. All necessary fluid reservoirs and pumps, calibrated for the current test fluid.

5. A continuous-wave argon-ion laser emitting light at 488 nm.

6. A CCD camera equipped with a Schott Optical Glass Long Pass Filter OG515.

7. A data acquisition system with the capability to synchronize the camera shutter to the impeller position.

The test is performed after filling the reactor with dyed fluid and activating the laser viewing plane. The agitator speed is set to the desired value (60 rpm in Experiment 1) and the experiment is enclosed in a black box to prevent the entry of laboratory light. Alternately, the test may be performed with the laboratory lights turned off. A series of initial images are captured and their average will be used as an initial calibration image.

The data acquisition system is started once more and, after a predetermined number of frames (4 in this case), the pump carrying undyed fluid is started at the desired flow rate (225 mL/min in this case). Images are captured once per revolution until the dye is completely washed from the tank. Since completing Experiment 1, we have standardized our procedure to require 6 reactor volumes of fluid (6×1.625 L=9.75 L of fluid for one experiment). Experiments with very low flow rate may be benefit from capturing images every 2 or more impeller revolutions to minimize the total data captured.

Once the experiment is complete, another set of images is collected to create a final calibration image. The impeller, pumps, and laser are turned off and the apparatus is ready for cleaning.

The images are processed by an initial normalization step and a subsequent correction. The normalization step is a linear interpolation wherein each pixel in the initial calibration image is taken as representing a normalized concentration of 1 and each pixel in the final calibration image is taken as representing a normalized concentration of 0. The subsequent correction accounts for the fact that the dye present in each frame slightly attenuates the laser plane and thus the laser intensity is not truly constant over the course of the experiment. This correction can be computed exactly by integrating the absorption along each laser ray, or a much simpler correction may be computed by using the average concentration in the integral (See J. P. Crimaldi, *Experiments in Fluids* 44, 851-863 (2008) for more details and the exact form of the integral).

Finally, the normalized intensity at each pixel location may be integrated over the course of the experiment to obtain a local age. This is done numerically by summing the images, beginning at the moment the pump was turned on. The result is a local fluid age distribution in one plane of the reactor in units of impeller revolutions. The data may be normalized to the measured or expected age of the fluid near the exit and it may be presented as a color-mapped image or as a histogram of local ages. Statistics such as the mean, standard deviation, and coefficient of variance (CoV) may be calculated.

INDUSTRIAL APPLICABILITY

The mean fluid age of the contents of a model of a CSTR can be determined relative to the exit age of the contents and can be used to determine for example which reactor ports to use, what agitator to use, what flow rates to use to improve reactor function.

The invention claimed is:

1. A method to determine a preferred inlet location for a continuous stirred tank reactor comprising:
   1) preparing a transparent model reactor comprising, an agitator, a number of alternate inlet ports, and at least one planar exterior surface, which model reactor will be used to generate data to be stored from subsequent steps of the method;
   2) filling the model reactor with a test fluid having a viscosity chosen to produce the desired Reynolds number, which fluid contains a uniform concentration of a tracer dye which fluoresces under a known wavelength of incident light;
   3) flowing six times the model reactor volume of test fluid without dye into and through the model reactor using a selected inlet port with the agitator running at a constant speed to provide a constant Reynolds number to introduce a step change in concentration of the tracer dye in the model reactor;
   4) while the dye is being washed out of the model reactor and during mixing, subjecting the model reactor contents to a plane of laser light through the planar exterior surface of the model reactor, whose wavelength causes the dye to fluoresce at a different wavelength from that of the laser;
   5) taking digital images of the fluorescent light from the model reactor through a filter to filter out the incident laser light at a rate synchronized with the rate of rotation of the agitator;
   6) calculating a normalized dye concentration in each pixel of each image;
   7) integrating the normalized concentration in each pixel over all images in time to calculate an average local fluid age of each pixel;
   8) calculating a standard deviation and a mean of the local ages and a coefficient of variance;
   9) iteratively repeating steps 1 through 8 for different inlets to the model reactor, wherein the calculated normalized dye concentration, calculated average local fluid age, calculated standard deviation and mean of the local ages, and calculated coefficient of variance become stored data;
   10) comparing the stored data to determine the inlet which provides at least one of:
      i) a normalized dye concentration from 0.5 to 1.3;
      ii) a coefficient of variance from 0.01 to 0.1; and
      iii) a minimum standard deviation in the average local age of the model reactor contents; and
      iv) a minimum standard deviation in the average age of the model reactor contents, and
   11) selecting the input port, which provides the preferred values from step 8.

2. A method to determine a preferred agitator for a continuous stirred tank reactor (CSTR) reactor comprising:
   1) preparing a transparent model reactor comprising, an agitator, a number of alternate inlet ports, and at least one planar exterior surface, which model reactor will be used to generate data to be stored from subsequent steps of the method;
   2) filling the model reactor with a test fluid having a viscosity chosen to produce the desired Reynolds number, which fluid contains a uniform concentration of a tracer dye which fluoresces under a known wavelength of incident light;
   3) flowing six times the model reactor volume of test fluid without dye into and through the model reactor using a selected inlet port and agitator running at a constant speed to provide a constant Reynolds number to introduce a step change in concentration of the tracer dye in the model reactor;
   4) while the dye is being washed out of the model reactor and during mixing, subjecting the model reactor contents to a plane of laser light through the planar exterior surface of the model reactor, whose wavelength causes the dye to fluoresce at a different wavelength from that of the laser;
   5) taking digital images of the fluorescent light from the model reactor through a filter to filter out the incident laser light at a rate synchronized with the rate of rotation of the agitator;
   6) calculating a normalized dye concentration in each pixel of each image;
   7) integrating the normalized concentration in each pixel over all images in time to calculate an average local fluid age of each pixel;
   8) calculating a standard deviation and a mean of the local ages and a coefficient of variance;
   9) iteratively repeating steps 1 through 8 for different agitators, wherein the calculated normalized dye concentration, calculated average local fluid age, calculated standard deviation and mean of the local ages, and calculated coefficient of variance become stored data;
   10) comparing the stored data to determine the agitator which provides at least one of:
      i) a normalized dye concentration from 0.5 to 1.3;
      ii) a coefficient of variance from 0.01 to 0.1; and
      iii) a minimum standard deviation in the average age of the model reactor contents, and
   11) selecting the agitator which provides the preferred values from step 8.

3. A method to determine a preferred feed flow rate to a continuous stirred tank reactor (CSTR) reactor comprising:
   1) preparing a transparent model reactor comprising, an agitator, a number of alternate inlet ports, and at least one planar exterior surface, which model reactor will be used to generate data to be stored from subsequent steps of the method;
   2) filling the model reactor with a test fluid having a viscosity chosen to produce the desired Reynolds number, which fluid contains a uniform concentration of a tracer dye which fluoresces under a known wavelength of incident light;
   3) flowing six times the model reactor volume of test fluid without dye into and through the model reactor at a constant flow rate using a selected feed port and agitator running at a constant speed to provide a constant Reynolds number to introduce a step change in concentration of the tracer dye in the model reactor;
   4) while the dye is being washed out of the model reactor and during mixing, subjecting the model reactor contents to a plane of laser light through the planar exterior surface of the model reactor, whose wavelength causes the dye to fluoresce at a different wavelength from that of the laser;
   5) taking digital images of the fluorescent light from the model reactor through a filter to filter out the incident laser light at a rate synchronized with the rate of rotation of the agitator;
   6) calculating a normalized dye concentration in each pixel of each image;

7) integrating the normalized concentration in each pixel over all images in time to calculate an average local fluid age of each pixel;
8) calculating a standard deviation and a mean of the local ages and a coefficient of variance;
9) iteratively repeating steps 1 through 8 for different feed flow rates to the model reactor, wherein the calculated normalized dye concentration, calculated average local fluid age, calculated standard deviation and mean of the local ages, and calculated coefficient of variance become stored data;
10) comparing the stored data to determine the model reactor feed rate which provides at least one of:
   i) a normalized dye concentration from 0.5 to 1.3;
   ii) a coefficient of variance from 0.01 to 0.1; and
   iii) a minimum standard deviation in the average age of the model reactor contents, and
11) selecting the model reactor feed rate which provides the preferred values from step 8.

4. A method to determine a preferred agitator speed for a continuous stirred tank reactor (CSTR) reactor comprising:
1) preparing a transparent model reactor comprising, an agitator, a number of alternate inlet ports, and at least one planar exterior surface, which model reactor will be used to generate data to be stored from subsequent steps of the method;
2) filling the model reactor with a test fluid having a viscosity chosen to produce the desired Reynolds number, which fluid contains a uniform concentration of a tracer dye which fluoresces under a known wavelength of incident light;
3) flowing six times the model reactor volume of test fluid without dye into and through the model reactor at a constant flow rate using a selected feed port and agitator running at a constant speed to provide a constant Reynolds number to introduce a step change in concentration of the tracer dye in the model reactor;
4) while the dye is being washed out of the model reactor and during mixing, subjecting the model reactor contents to a plane of laser light through the planar exterior surface of the model reactor, whose wavelength causes the dye to fluoresce at a different wavelength from that of the laser;
5) taking digital images of the fluorescent light from the model reactor through a filter to filter out the incident laser light at a rate synchronized with the rate of rotation of the agitator;
6) calculating a normalized dye concentration in each pixel of each image;
7) integrating the normalized concentration in each pixel over all images in time to calculate an average local fluid age of each pixel;
8) calculating a standard deviation and a mean of the local ages and a coefficient of variance;
9) iteratively repeating steps 1 through 8 for different agitator speeds, wherein the calculated normalized dye concentration, calculated average local fluid age, calculated standard deviation and mean of the local ages, and calculated coefficient of variance become stored data;
10) comparing the stored data to determine the agitator speed which provides at least one of:
   i) a normalized dye concentration from 0.5 to 1.3;
   ii) a coefficient of variance from 0.01 to 0.1; and
   iii) a minimum standard deviation in the average age of the model reactor contents, and
11) selecting the agitator speed which provides the preferred values from step 8.

5. The method of claim 1, wherein the agitator is selected from the group consisting of auger agitators, anchor agitators, radial blade turbine, pitched blade turbine, hydrofoil impeller, or a hybrid impeller comprising one or more of these elements.

6. The method of claim 1, wherein the continuous stirred tank reactor is used for a polymerization process.

7. The method of claim 1, wherein the test fluid is liquid.

8. The method of claim 7 wherein the liquid is selected from the group consisting of one or more $C_{5-12}$.

9. The method of claim 8, wherein the coefficient of variance, which is defined as the standard deviation/mean, is from 0.01 to 0.10.

10. The method of claim 8, wherein the coefficient of, which is defined as the standard deviation/mean, is from 0.01 to 0.06.

11. The method of claim 6, wherein the local age of the continuous stirred tank reactor contents normalized to the exit age is from 0.6 to 1.2.

12. The method of claim 7, wherein the average normalized fluid age in the continuous stirred tank reactor is from 0.8 to 1.0.

* * * * *